US010676450B2

(12) United States Patent
Schmidt et al.

(10) Patent No.: US 10,676,450 B2
(45) Date of Patent: Jun. 9, 2020

(54) PROCESS FOR THE EPOXIDATION OF AN OLEFIN

(71) Applicants: EVONIK DEGUSSA GMBH, Essen (DE); THYSSENKRUPP INDUSTRIAL SOLUTIONS AG, Essen (DE)

(72) Inventors: Franz Schmidt, Frankfurt (DE); Nico Dauth, Langenselbold (DE); Matthias Pascaly, Frankfurt (DE)

(73) Assignees: EVONIK OPERATIONS GMBH, Essen (DE); THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 16/070,873

(22) PCT Filed: Jan. 6, 2017

(86) PCT No.: PCT/EP2017/050236
§ 371 (c)(1),
(2) Date: Jul. 18, 2018

(87) PCT Pub. No.: WO2017/125266
PCT Pub. Date: Jul. 27, 2017

(65) Prior Publication Data
US 2019/0023673 A1 Jan. 24, 2019

(30) Foreign Application Priority Data
Jan. 19, 2016 (EP) .................................... 16151786

(51) Int. Cl.
*C07D 301/12* (2006.01)
*B01J 29/89* (2006.01)
*C07B 41/04* (2006.01)
*C07D 303/04* (2006.01)
*B01J 19/24* (2006.01)

(52) U.S. Cl.
CPC ............ *C07D 301/12* (2013.01); *B01J 29/89* (2013.01); *C07B 41/04* (2013.01); *C07D 303/04* (2013.01); *B01J 19/2415* (2013.01)

(58) Field of Classification Search
CPC ................................................... C07D 301/12
USPC ........................................................ 549/531
See application file for complete search history.

(56) References Cited

U.S. PATENT DOCUMENTS

| 4,308,409 | A | 12/1981 | Wu et al. |
| 5,274,140 | A | 12/1993 | Venturello et al. |
| 5,591,875 | A * | 1/1997 | Chang .................. C07D 301/12 549/531 |
| 5,599,956 | A | 2/1997 | Pujado et al. |
| 6,372,924 | B2 | 4/2002 | Thiele |
| 6,673,950 | B1 | 1/2004 | Teles et al. |
| 6,861,042 | B2 | 3/2005 | Korl et al. |
| 7,169,945 | B2 * | 1/2007 | Haas .................... C07D 301/12 549/531 |
| 7,173,143 | B2 | 2/2007 | Bender et al. |
| 7,601,263 | B2 | 10/2009 | Ebert et al. |
| 7,658,893 | B2 | 2/2010 | Bassler et al. |
| 7,670,572 | B2 | 3/2010 | Porscha et al. |
| 7,833,498 | B2 | 11/2010 | Goebbel et al. |
| 7,863,211 | B2 | 1/2011 | Strebelle et al. |
| 8,545,673 | B2 | 10/2013 | Dietz et al. |
| 9,539,549 | B2 | 1/2017 | Haensel et al. |
| 10,053,438 | B2 | 8/2018 | Boltz et al. |
| 10,053,440 | B2 | 8/2018 | Boltz et al. |
| 10,087,158 | B2 | 10/2018 | Stock et al. |
| 10,100,024 | B2 | 10/2018 | Stochniol et al. |
| 10,125,108 | B2 | 11/2018 | Jahn et al. |
| 10,214,471 | B2 | 2/2019 | Wiederhold et al. |
| 10,214,504 | B2 | 2/2019 | Brendel et al. |
| 10,399,952 | B2 | 9/2019 | Wöll |
| 2003/0040637 | A1 | 2/2003 | Hofen et al. |
| 2005/0245751 | A1 | 11/2005 | Bender et al. |
| 2006/0014970 | A1 | 1/2006 | Goebbel et al. |
| 2006/0058539 | A1 | 3/2006 | Babler et al. |
| 2007/0004926 | A1 | 1/2007 | Schindler et al. |
| 2012/0142950 | A1 | 6/2012 | Teles et al. |
| 2015/0007951 | A1 | 1/2015 | Dietz et al. |
| 2017/0210718 | A1 | 7/2017 | Stochinol et al. |

(Continued)

FOREIGN PATENT DOCUMENTS

| DE | 195 07 584 | 9/1996 |
| EP | 0 100 119 | 2/1984 |

(Continued)

OTHER PUBLICATIONS

International Search Report for PCT/EP2017/050236 filed Jan. 6, 2017.
Written Opinion of the International Searching Authority for PCT/EP2017/050236 filed Jan. 6, 2017.
International Preliminary Report on Patentability for PCT/EP2017/050236 filed Jan. 6, 2017.
International Search Report for PCT/EP2016/076268 filed Nov. 1, 2016, for copending U.S. Appl. No. 15/778,337.
Written Opinion of the International Searching Authority for PCT/EP2016/076268 filed Nov. 1, 2016, for copending U.S. Appl. No. 15/778,337.

(Continued)

*Primary Examiner* — Nizal S Chandrakumar
(74) *Attorney, Agent, or Firm* — Law Office of: Michael A. Sanzo, LLC

(57) ABSTRACT

In a process for the epoxidation of an olefin with hydrogen peroxide in the presence of a solvent, where a mixture comprising olefin, an aqueous hydrogen peroxide solution and a solvent is continuously passed through a fixed bed of an epoxidation catalyst comprising a titanium zeolite, addition of a chelating agent to the aqueous hydrogen peroxide solution before mixing it with solvent reduces or prevents formation of deposits on the catalyst and blocking of orifices of a liquid distributor.

16 Claims, No Drawings

(56) References Cited

U.S. PATENT DOCUMENTS

| | | |
|---|---|---|
| 2018/0002299 A1 | 1/2018 | Bolz et al. |
| 2018/0002300 A1 | 1/2018 | Bolz et al. |
| 2018/0030010 A1 | 2/2018 | Breitenbach et al. |
| 2018/0030011 A1 | 2/2018 | Stock et al. |
| 2018/0030012 A1 | 2/2018 | Stock et al. |
| 2018/0057473 A1 | 3/2018 | Stock et al. |
| 2018/0134676 A1 | 5/2018 | Jahn et al. |
| 2018/0346432 A1 | 12/2018 | Hofen et al. |
| 2018/0354878 A1 | 12/2018 | Wiederhold et al. |
| 2018/0354923 A1 | 12/2018 | Pascaly et al. |
| 2018/0370934 A1 | 12/2018 | Brendel et al. |

FOREIGN PATENT DOCUMENTS

| | | |
|---|---|---|
| EP | 0 230 949 | 8/1987 |
| EP | 0 659 473 | 6/1995 |
| EP | 0 757 045 | 2/1997 |
| EP | 1 247 806 | 10/2002 |
| EP | 1 489 074 | 12/2004 |
| WO | WO 02/085873 | 10/2002 |
| WO | WO 03/016296 | 2/2003 |
| WO | WO 03/018567 | 3/2003 |
| WO | WO 03/093255 | 11/2003 |
| WO | WO 2004/018088 | 3/2004 |
| WO | WO 2004/028962 | 4/2004 |
| WO | WO 2004/048335 | 6/2004 |
| WO | WO 2004/048354 | 6/2004 |
| WO | WO 2004/048355 | 6/2004 |
| WO | WO 2005/000827 | 1/2005 |
| WO | WO 2005/103024 | 11/2005 |
| WO | WO 2008/141734 | 11/2008 |
| WO | WO 2011/063937 | 6/2011 |
| WO | WO 2016/016070 | 2/2016 |

OTHER PUBLICATIONS

International Preliminary Report on Patentability for PCT/EP2016/076268 filed Nov. 1, 2016 for copending U.S. Appl. No. 15/778,337.
European Search Report for EP 15 19 6528 filed Nov. 26, 2015 corresponding to PCT/EP2016/076268 filed Nov. 1, 2016, for copending U.S. Appl. No. 15/778,337.
Chowdhury, et al, "Recovery of Homogeneous Polyoxometallate Catalysts from Aqueous and Organic Media by a Mesoporous Ceramic Membrane without Loss of Catalytic Activity," *Chem. Eur. J.* 12(11):3061-3066 (Apr. 2006).
Guojie, et al., "Factors Affecting Propylene Epoxidation Catalyzed by Reaction-Controlled Phase-Transfer Catalyst," *Chinese Journal of Catalysis* 26:1005-1010 (Nov. 2005).
Kaur, et al., "Poloxometalate-catalysed epoxidation of propylene with hydrogen peroxide: microemulsion versus biphasic process," *Catalysis Communications* 5(11): 709-713 (Nov. 2004).
Li, et al., "Influence of composition of heteropolyphosphatotungstate catalyst on epoxidation of propylene," *Journal of Molecular Catalysis A: Chemical* 218(2):247-252 (Aug. 2004).
Luthra, et al., "Homogeneous phase transfer catalyst recovery and re-use using solvent resistant membranes," *Journal of Membrane Science* 201:65-75 (2002).
Venturello, et al., "A New, Effective Catalytic System for Epoxidation of Olefins by Hydrogen Peroxide under Phase-Transfer Conditions," *J. Org. Chem.* 48:3831-3833 (1983).
U.S. Appl. No. 15/329,626, filed Jan. 26, 2017, US-2017/0210718 A1, Jul. 27, 2017, Stochinol.
U.S. Appl. No. 15/570,167, filed Oct. 15, 2017, US-2018/0134676 A1, May 27, 2018, Jahn.
U.S. Appl. No. 15/778,318, filed May 23, 2018, Brendel.
U.S. Appl. No. 15/778,425, filed May 23, 2018, Hofen.
U.S. Appl. No. 15/778,562, filed May 23, 2018, Wiederhold.
U.S. Appl. No. 15/778,337, filed May 23, 2018, Pascaly.
Office Action for copending U.S. Appl. No. 15/778,337 dated Nov. 26, 2018.
Ullmanns Encyclopedia of Industrial Chemistry, online edition 2013, entry "propene," DOI 10.1002/14356007.a22_211.pub3.
U.S. Appl. No. 16/086,309, filed Sep. 18, 2018, Wöll.
U.S. Appl. No. 16/302,099, filed Nov. 15, 2018, Wiederhold.
Response to Office Action for copending U.S. Appl. No. 15/778,337, filed Feb. 25, 2019.
Notice of Allowance for copending U.S. Appl. No. 15/778,337 dated May 16, 2019.
Shin, et al., "Kinetics of Heterogeneous Catalytic Epoxidation of Propene with Hydrogen Peroxide over Titanium Silicalite (TS-1)," *Ind. Eng. Chem. Res.* 49:8125-8134 (published on Web Jul. 27, 2010).
Wang, et al., "Epoxidation of Propylene Over Titanosilicate-1 in Fixed-bed Reactor: Experiments and Kinetics," *Asian Journal of Chemistry* 26(4) :9430950 (published online Feb. 15, 2014).

* cited by examiner

PROCESS FOR THE EPOXIDATION OF AN OLEFIN

CROSS REFERENCE TO RELATED APPLICATIONS

The present application is US national stage of international application PCT/EP2017/050236, which had an international filing date of Jan. 6, 2017 and which was published on Jul. 27, 2017. Priority is claimed to European application EP 16151786.7, filed on Jan. 19, 2016.

FIELD OF THE INVENTION

The present invention relates to a process for the epoxidation of an olefin in which a mixture comprising olefin, hydrogen peroxide and a solvent is continuously passed through a fixed bed of an epoxidation catalyst comprising a titanium zeolite.

BACKGROUND OF THE INVENTION

The liquid phase epoxidation of olefins with hydrogen peroxide catalyzed by a fixed bed titanium silicalite catalyst is known from EP 0 100 119 A1. The reaction is usually carried out in a methanol solvent to achieve high reaction rate and product selectivity. Continuous epoxidation is achieved by passing a mixture comprising olefin, hydrogen peroxide and methanol through a fixed bed of the epoxidation catalyst, as described in WO 99/28029, WO 01/10855 and EP 1 085 017 A1.

EP 757 045 A1 teaches that in an epoxidation process where an olefin is reacted with hydrogen peroxide in the presence of a titanium-containing molecular sieve catalyst and a salt, the tendency of the catalyst to produce oxygen as it ages due to non-selective decomposition of the hydrogen peroxide may be counteracted by the addition of a chelating agent. Polyphosphonic acids as well as their alkali metal, alkaline earth metal and ammonium salts may be used as chelating agents. EP 757 045 A1 discloses an epoxidation of propene in a continuous stirred tank reactor using an extrudate containing TS-1 titanium silicalite, where aminotrimethylenephosphonic acid is added to a feed stream containing 2.5% by weight hydrogen peroxide, 73% by weight isopropanol, 24% by weight water, 0.2% by weight methanol, 0.29% by weight acetic acid and 0.1% by weight formic acid.

SUMMARY OF THE INVENTION

It has now been found that during extended operation of such a continuous epoxidation, deposits can form on the catalyst which are not removed by usual catalyst regeneration procedures of washing with a solvent or heating. These deposits reduce catalyst activity and may cause liquid maldistribution in the catalyst fixed bed, leading to an uneven temperature profile in the fixed bed which impairs selectivity for the epoxide. When a tube bundle reactor is used and a mixture comprising hydrogen peroxide and solvent is distributed to the tubes through orifices of a liquid distributor, similar deposits can form or accumulate at the orifices and blocking of the orifices by the deposits can lead to maldistribution of liquid to the individual tubes.

It has further been found that formation of such deposits may be reduced or avoided by adding a chelating agent to the aqueous hydrogen peroxide solution before mixing it with solvent.

Subject of the invention is therefore a process for the epoxidation of an olefin with hydrogen peroxide in the presence of a solvent, wherein hydrogen peroxide is used as an aqueous hydrogen peroxide solution, a chelating agent is added to the aqueous hydrogen peroxide solution before it is mixed with solvent, and a mixture comprising olefin, solvent and hydrogen peroxide with added chelating agent is continuously passed through a fixed bed of an epoxidation catalyst comprising a titanium zeolite.

DETAILED DESCRIPTION OF THE INVENTION

In the process of the invention, a mixture comprising olefin, hydrogen peroxide and a solvent is continuously passed through a fixed bed of an epoxidation catalyst comprising a titanium zeolite.

The olefin is preferably an unbranched olefin, more preferably an unbranched C2-C6 olefin. The olefin may be substituted, as for example in allyl chloride. Most preferably, the olefin is propene. Propene may be used mixed with propane, preferably with a molar ratio of propane to propene of from 0.001 to 0.15 and more preferably of from 0.08 to 0.12.

The hydrogen peroxide used in the process of the invention is an aqueous hydrogen peroxide solution. The aqueous hydrogen peroxide solution preferably has a hydrogen peroxide concentration of from 20 to 85% by eight, more preferably 40 to 70% by weight. The combined amount of water and hydrogen peroxide is preferably higher than 95% by weight, more preferably higher than 99% by weight. The aqueous hydrogen peroxide solution preferably comprises phosphoric acid or an alkali metal or ammonium salt of phosphoric acid, and most preferably comprises phosphoric acid in a concentration of from 50 to 1000 ppm by weight. The aqueous hydrogen peroxide solution may also comprise pyrophosphoric acid or an alkali metal or ammonium salt of pyrophosphoric acid.

The aqueous hydrogen peroxide solution is preferably made by an anthraquinone process. The anthraquinone process uses a working solution comprising at least one 2-alkylanthraquinone, 2-alkyltetrahydroanthraquinone or a mixture of both, referred to as quinones in the following, and at least one solvent for dissolving the quinone and the hydroquinone. The 2-alkylanthraquinone is preferably 2-ethylanthraquinone (EAQ), 2-amylanthraquinone (AAQ) or 2-(4-methylpentyl)-anthraquinone (IHAQ) and more preferably a mixture of EAQ with AAQ and/or IHAQ where the molar fraction of quinones carrying an ethyl group is from 0.05 to 0.95. The working solution preferably further comprises the corresponding 2-alkyltetrahydroanthraquinones and the ratio of 2-alkyltetrahydroanthraquinones plus 2-alkyltetrahydroanthrahydroquinones to 2-alkylanthraquinones plus 2-alkylanthrahydroquinones is preferably maintained in the range of from 1 to 20 by adjusting the conditions of the hydrogenating and regenerating steps used in the anthraquinone process. The working solution preferably comprises a mixture of alkylbenzenes having 9 or 10 carbon atoms as solvent for anthraquinones and at least one polar solvent selected from diisobutylcarbinol (DiBC), methylcyclohexylacetate (MCA), trioctylphosphate (TOP), tetrabutylurea (TBU) and N-octylcaprolactam as solvent for anthrahydroquinones, DiBC, MCA and TOP being preferred and TOP being most preferred.

The anthraquinone process is a cyclic process, comprising a hydrogenation stage, where hydrogen is reacted with working solution in the presence of a hydrogenation catalyst to convert at least part of the quinone to the corresponding hydroquinone, a subsequent oxidation stage, where the hydrogenated working solution containing hydroquinone is reacted with oxygen to form hydrogen peroxide and quinone, and an extraction stage, where hydrogen peroxide is extracted from the oxidized working solution with water to provide an aqueous solution of hydrogen peroxide, with the extracted working solution being returned to the hydrogenation stage to complete a reaction cycle.

In the hydrogenation stage, the working solution is reacted with hydrogen in the presence of a heterogeneous hydrogenation catalyst. During the reaction all or a part of the quinones are converted to the corresponding hydroquinones. All hydrogenation catalysts known from the prior art for the anthraquinone cyclic process can be used as catalysts in the hydrogenation stage. Noble metal catalysts containing palladium as the principal component are preferred. The catalysts can be used as a fixed bed catalysts or as a suspended catalyst and suspended catalysts can be either unsupported catalysts, such as palladium black, or supported catalysts, with suspended supported catalysts being preferred. $SiO_2$, $TiO_2$, $Al_2O_3$ and mixed oxides thereof, as well as zeolites, $BaSO_4$ or polysiloxanes, are can be used as support materials for fixed-bed catalysts or supported suspended catalysts, with $TiO_2$ and $SiO_2/TiO_2$ mixed oxides being preferred. Catalysts in the form of monolithic or honeycombed moldings, the surface of which is coated with the noble metal, can also be used. Hydrogenation can be carried out in stirred-tank reactors, tube reactors, fixed-bed reactors, loop reactors or air-lift reactors which can be equipped with devices for distributing hydrogen in the working solution, such as static mixers or injection nozzles. Preferably, a tube reactor with a recycle and a Venturi nozzle for injecting hydrogen into the reactor feed as known from WO 02/34668 is used. Hydrogenation is carried out at a temperature of from 20 to 100° C., preferably 45 to 75° C., and a pressure of from 0.1 MPa to 1 MPa, preferably 0.2 MPa to 0.5 MPa. The hydrogenation is preferably performed in such a way that essentially all hydrogen introduced into the hydrogenation reactor is consumed in a single pass through the reactor. The ratio between hydrogen and working solution fed to the hydrogenation reactor is preferably chosen to convert between 30 and 80% of the quinones to the corresponding hydroquinones. If a mixture of 2-alkylanthraquinones and 2-alkyltetrahydroanthraquinones is used, the ratio between hydrogen and working solution is preferably chosen so that only the 2-alkyltetrahydroanthraquinones are converted to hydroquinones and the 2-alkylanthraquinones remain in the quinone form.

In the oxidation stage, the hydrogenated working solution from is reacted with an oxygen-containing gas, preferably with air or with oxygen enriched air. All oxidation reactors known from the prior art for the anthraquinone process can be used for the oxidation, bubble columns operated in co-current being preferred. The bubble column can be free from internal devices, but preferably contains distribution devices in the form of packings or sieve plates, most preferably sieve plates in combination with internal coolers. Oxidation is carried out at a temperature of from 30 to 70° C., preferably from 40 to 60° C. Oxidation is preferably performed with an excess of oxygen to convert more than 90%, preferably more than 95%, of the hydroquinones to the quinone form.

In the extraction stage, the oxidized working solution containing dissolved hydrogen peroxide is extracted with an aqueous solution to provide an aqueous hydrogen peroxide solution and an extracted oxidized working solution containing essentially no hydrogen peroxide. Deionized water, which may optionally contain additives for stabilizing hydrogen peroxide, adjusting the pH and/or corrosion protection, is preferably used for extracting the hydrogen peroxide. The aqueous solution used for extracting hydrogen peroxide from the working solution preferably comprises phosphoric acid in a concentration of from 50 to 500 ppm by weight. Extraction is preferably carried out in a countercurrent continuous extraction column, sieve-plate columns being most preferred. The aqueous hydrogen peroxide solution obtained by extraction may be used directly in the epoxidation or may be concentrated by distilling off water at reduced pressure, preferably to a concentration of from 40 to 70% by weight. The aqueous hydrogen peroxide solution obtained by extraction may also be purified, preferably by washing with a solvent, which is preferably a solvent comprised in the working solution.

The anthraquinone process preferably comprises at least one additional stage for regenerating the working solution, where by-products formed in the process are converted back to quinones.

Regeneration is carried out by treating hydrogenated working solution with alumina or sodium hydroxide, preferably using a side stream to the cyclic process. In addition to regeneration of hydrogenated working solution, extracted oxidized working solution may be regenerated in a side stream using alumina, sodium hydroxide or an organic amine. Suitable methods for regenerating the working solution on an anthraquinone process are known from the prior art.

In the process of the invention, the olefin is reacted with hydrogen peroxide in a solvent. Suitable are all solvents which are not oxidized or are oxidized to only a small extent by hydrogen peroxide under the reaction conditions chosen and which dissolve in water in an amount of more than 10% by weight. Solvents which are completely miscible with water are preferred. Suitable solvents are alcohols, such as methanol, ethanol or tert-butanol; glycols, such as ethylene glycol, 1,2-propanediol or 1,3-propanediol; cyclic ethers, such tetrahydrofuran, dioxane or propylene oxide; glycol ethers, such ethylene glycol monomethyl ether, ethylene glycol monoethyl ether, ethylene glycol monobutyl ether or the propylene glycol monomethyl ethers; ketones, such as acetone or 2-butanone; and nitriles, such as acetonitrile and proprionitrile. Preferably, the solvent is a methanol solvent. The methanol solvent can be a technical grade methanol, a methanol solvent stream recovered in the work-up of the epoxidation reaction mixture or a mixture of both. The methanol solvent may comprise other solvents in minor amounts, such as ethanol, with the amount of such other solvents preferably being less than 2% by weight. The solvent is preferably used in the epoxidation in a weight ratio of 0.5 to 20 relative to the combined weight of water and hydrogen peroxide.

The olefin is preferably used at a molar ratio of olefin to hydrogen peroxide of from 1.1:1 to 30:1, more preferably 2:1 to 10:1 and most preferably 3:1 to 5:1. The epoxidation reaction is preferably carried out at a temperature of 20 to 80° C., more preferably at 25 to 60° C. The epoxidation reaction is preferably carried out at a pressure that is higher than the vapor pressure of the olefin at the reaction temperature in order to maintain the olefin dissolved in the solvent or present as a separate liquid phase. The epoxidation reaction is preferably carried out with addition of ammonia to improve epoxide selectivity as described in EP 0 230 949 A2. Ammonia is preferably added in an amount of from 100 to 3000 ppm based on the weight of hydrogen peroxide.

When the olefin is propene, the pressure in the epoxidation reaction is preferably from 1.9 to 5.0 MPa, more preferably 2.1 to 3.6 MPa and most preferably 2.4 to 2.8 MPa. Propene is preferably used in an excess sufficient to maintain an additional liquid phase rich in propene throughout the epoxidation reaction. Using an excess of propene at a high pressure provides high reaction rate and hydrogen peroxide conversion and at the same time high selectivity for propene oxide.

The mixture comprising olefin, hydrogen peroxide and a solvent is continuously passed through a fixed bed of an epoxidation catalyst comprising a titanium zeolite. Suitable titanium zeolites contain titanium atoms on silicon lattice positions. Preferably, a titanium silicalite catalyst is used, preferably with an MFI or MEL crystal structure. Most preferably a titanium silicalite 1 catalyst with MFI structure as known from EP 0 100 119 A1, is used. The titanium silicalite catalyst is preferably employed as a shaped catalyst in the form of granules, extrudates or shaped bodies. The shaped catalyst may contain 1 to 99% of a binder or carrier material, all binders and carrier materials being suitable that do not react with hydrogen peroxide or with propene oxide under the reaction conditions employed for the epoxidation, silica being preferred as binder. Extrudates with a diameter of 1 to 5 mm are preferably used as fixed bed catalysts. The amount of catalyst employed may be varied within wide limits and is preferably chosen so that a hydrogen peroxide consumption of more than 90%, preferably more than 95%, is achieved within 1 minute to 5 hours under the employed epoxidation reaction conditions.

The epoxidation is preferably carried out in a fixed bed reactor equipped with cooling means and cooled with a liquid cooling medium. When the olefin is propene, the temperature profile along the length of the catalyst fixed bed is preferably adjusted to keep the reaction temperature along 70 to 98%, preferably along 80 to 95%, of the length of the catalyst fixed bed within a range of less than 5° C., preferably within a range of from 0.5 to 3° C. The temperature of the cooling medium fed to the cooling means is preferably adjusted to a value 3 to 13° C. lower than the maximum temperature in the catalyst fixed bed. The epoxidation reaction mixture is preferably passed through the catalyst bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst bed. Additionally it is preferred to pass the reaction mixture through the catalyst bed with a liquid hourly space velocity (LHSV) from 1 to 20 $h^{-1}$, preferably 1.3 to 15 $h^{-1}$. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15. When the olefin is propene, the epoxidation reaction is most preferably carried out with a catalyst fixed bed maintained in a trickle bed state at a pressure close to the vapor pressure of propene at the reaction temperature, using an excess of propene that provides a reaction mixture comprising two liquid phases, a solvent rich phase and a propene rich liquid phase. Two or more fixed bed reactors may be operated in parallel or in series in order to be able to operate the epoxidation process continuously when regenerating the epoxidation catalyst. Regeneration of the epoxidation catalyst can be carried out by calcination, by treatment with a heated gas, preferably an oxygen containing gas or by a solvent wash, preferably by the periodic regeneration described in WO 2005/000827. Different methods of regeneration may also be combined.

In the process of the invention, a chelating agent is added to the aqueous hydrogen peroxide solution before is mixed with solvent. The chelating agent is preferably added before the aqueous hydrogen peroxide solution is mixed with at least 50% of the solvent used for reacting the olefin with hydrogen peroxide, more preferably with at least 80% of the solvent. In principle, any compound capable of coordinating to a $Fe^{3+}$ ion through at least two coordinating atoms can be used as chelating agent. Preferably, a hydroxycarboxylic acid, i.e. a compound containing a carboxylic acid group and a hydroxyl group on the same or on neighbouring carbon atoms, a polycarboxylic acid, i.e. a compound comprising at least two carboxylic acid groups, or a polyphosphonic acid, i.e. a compound comprising at least two phosphonic acid groups, or an alkali metal or ammonium salt of a hydroxycarboxylic acid, a polycarboxylic acid or a polyphosphonic acid is used as chelating agent. Polyphosphonic acids and their alkali metal and ammonium salts are particularly preferred, and polyphosphonic acids are most preferred. Suitable hydroxycarboxylic acid and polycarboxylic acid chelating agents are malic acid, gluconic acid, tartaric acid, citric acid, oxalic acid, succinic acid, iminodisuccinic acid, β-alaninediacetic acid, methylglycinediacetic acid, nitrilotriacetic acid and ethylenediaminetetraacetic acid. Suitable polyphosphonic acid chelating agents are 1-hydroxyethane-1,1-diphosphonic acid (HEDP), amino-tris(methylenephosphonic acid) (ATMP), ethylenediaminetetra(methylenephosphonic acid) (EDTMP) and diethylenetriaminepenta (methylenephosphonic acid) (DTPMP), with HEDP being most preferred.

The chelating agent is preferably added in an amount of from $10^{-7}$ to $10^{-2}$ mol chelating agent per mol of hydrogen peroxide.

Adding a chelating agent to the aqueous hydrogen peroxide solution before mixing it with solvent reduces or prevents the formation of poorly soluble deposits on the titanium zeolite epoxidation catalyst which reduce catalyst activity and may cause liquid maldistribution in the catalyst fixed bed. It also reduces or prevents a blocking of orifices of a liquid distributor used for distributing the aqueous hydrogen peroxide to tubes of a tube bundle reactor used for the epoxidation reaction, which blocking would lead to maldistribution of liquid to the individual tubes. Adding a chelating agent is particularly effective for preventing the formation of deposits resulting from metal impurities in the starting materials, such as deposits of metal hydroxides and hydrous oxides or deposits of metal phosphates.

The mixture resulting from mixing solvent and aqueous hydrogen peroxide solution with added chelating agent is preferably mixed with the olefin before being contacted with the fixed bed epoxidation catalyst. Mixing may be carried out by turbulent flow in a feed line or in a dedicated mixer, such as a static mixer. Mixing may also be achieved by passing the mixture, the olefin and optionally further feed streams through a layer of inert solid, such as a layer of glass beads, arranged upstream of the fixed bed epoxidation catalyst.

In a preferred embodiment of the invention, the fixed bed epoxidation catalyst is placed in the tubes of a vertically arranged tube bundle reactor, chelating agent is added to an aqueous hydrogen peroxide stream before it is mixed with a solvent stream to form a mixed stream, and the mixed stream is distributed to the top of the tubes through orifices of a liquid distributor. The flow rates of the streams and reaction conditions are preferably selected to maintain the catalyst bed in a trickle bed state as described above. Suitable liquid distributors are known from the prior art and are commercially available. The mixed stream may be combined with the olefin before it is distributed to the top of the tubes, which is preferred if the mixture resulting from combining the mixed stream with the olefin forms a single liquid phase. Alternatively, the mixed stream and the olefin may be distributed to the top of the tubes through orifices of two separate liquid distributors, which is preferred when the olefin is employed in an amount exceeding its solubility in the mixed stream. Suitable liquid distributors for separately distributing two liquids to reaction tubes of a tube bundle reactor are known from the prior art, for example from WO 2005/025716.

The olefin oxide formed by the epoxidation reaction can be separated from the epoxidation reaction mixture by methods known from the prior art, such as by distillation or extractive distillation. When the olefin is propene and the solvent is a methanol solvent, propene oxide is preferably separated from the epoxidation reaction mixture by distillation after a pressure release stage which removes most of the non-reacted propene. The distillation is preferably carried out in at least two columns, operating the first column to provide a crude propene oxide overhead product containing from 20 to 60% of the methanol contained in the epoxidation reaction mixture and further purifying the overhead product by at least one additional distillation. The overhead product is preferably further purified by distilling off remaining propene and propane, followed by extractive distillation, most preferably using the extractive distillation method of WO 2004/048355 for additional removal of carbonyl compounds.

EXAMPLES

Example 1 (Comparative)

500 g of a 57% by weight aqueous hydrogen peroxide solution containing 436 mg/kg iron (III) chloride (150 mg/kg $Fe^{3+}$) was mixed with a methanol solvent consisting of 1900 g methanol, 150 g water and 850 mg ammonia. A solid precipitated, which was filtered, dried and weighed. The dried precipitate weighed 226 mg.

Example 2

Example 1 was repeated, but 50 g of a 1% by weight aqueous solution of HEDP was added to the aqueous hydrogen peroxide solution before it was mixed with the methanol solvent. A solid precipitated, which was filtered, dried and weighed. The dried precipitate weighed 39 mg.

The example demonstrates that addition of the chelating agent to the aqueous hydrogen peroxide solution strongly reduces precipitate formation from iron salt impurities.

Example 3 (Comparative)

Example 2 was repeated, but the aqueous solution of HEDP was added after mixing the aqueous hydrogen peroxide solution with the methanol solvent instead of adding it to the aqueous hydrogen peroxide solution. A solid precipitated, which was filtered, dried and weighed. The dried precipitate weighed 135 mg.

The example demonstrates that adding the chelating agent after mixing the aqueous hydrogen peroxide solution with the solvent is less efficient than adding the chelating agent to the aqueous hydrogen peroxide solution before mixing it with the solvent.

Example 4 (Comparative)

Example 2 was repeated, but the aqueous solution of HEDP was added to the methanol solvent before it was mixed with the aqueous hydrogen peroxide solution instead of adding it to the aqueous hydrogen peroxide solution. A solid precipitated, which was filtered, dried and weighed. The dried precipitate weighed 130 mg.

The example demonstrates that adding the chelating agent to the solvent is less efficient than adding the chelating agent to the aqueous hydrogen peroxide solution.

Example 5

Example 2 was repeated, but 875 mg citric acid was added to the aqueous hydrogen peroxide solution instead of the aqueous solution of HEDP. A solid precipitated, which was filtered, dried and weighed. The dried precipitate weighed 118 mg.

Example 6 (Comparative)

Example 1 was repeated with an aqueous hydrogen peroxide solution containing 572 mg/kg aluminum (III) nitrate nonahydrate (72.5 mg/kg $Al^{3+}$) instead of the iron (III) chloride. A solid precipitated, which was filtered, dried and weighed. The dried precipitate weighed 67 mg.

Example 7

Example 6 was repeated, but 50 g of a 1% by weight aqueous solution of HEDP was added to the aqueous hydrogen peroxide solution before it was mixed with the methanol solvent. No solid precipitated.

The example demonstrates that addition of the chelating agent to the aqueous hydrogen peroxide solution prevents precipitate formation from aluminum salt impurities.

Example 8 (Comparative)

500 g of a 57% by weight aqueous hydrogen peroxide solution containing 436 mg/kg iron (III) chloride (150 mg/kg $Fe^{3+}$) was mixed with an acetonitrile solvent consisting of 1900 g acetonitrile, 150 g water and 850 mg ammonia. A solid precipitated, which was filtered, dried and weighed. The dried precipitate weighed 27 mg.

Example 9

Example 8 was repeated, but 50 g of a 1% by weight aqueous solution of HEDP was added to the aqueous hydrogen peroxide solution before it was mixed with the acetonitrile solvent. A solid precipitated, which was filtered, dried and weighed. The dried precipitate weighed 23 mg.

Example 10 (Comparative)

Example 1 was repeated, but an ethanol solvent consisting of 1900 g ethanol, 150 g water and 850 mg ammonia was used instead of the methanol solvent. A solid precipitated, which was filtered, dried and weighed. The dried precipitate weighed 123 mg.

Example 11

Example 10 was repeated, but 50 g of a 1% by weight aqueous solution of HEDP was added to the aqueous hydrogen peroxide solution before it was mixed with the ethanol solvent. A solid precipitated, which was filtered, dried and weighed. The dried precipitate weighed 77 mg.

Example 12 (Comparative)

Example 1 was repeated, but a 2-propanol solvent consisting of 1900 g 2-propanol, 150 g water and 850 mg ammonia was used instead of the methanol solvent. A solid precipitated, which was filtered, dried and weighed. The dried precipitate weighed 57 mg.

Example 13

Example 12 was repeated, but 50 g of a 1% by weight aqueous solution of HEDP was added to the aqueous hydrogen peroxide solution before it was mixed with the 2-propanol solvent. A solid precipitated, which was filtered, dried and weighed. The dried precipitate weighed 48 mg.

Examples 8 to 13 demonstrate that addition of the chelating agent to the aqueous hydrogen peroxide solution reduces precipitate formation from iron salt impurities for different types of solvent.

The invention claimed is:

1. A process for the epoxidation of an olefin with hydrogen peroxide in the presence of a solvent, wherein the solvent is selected from the group consisting of methanol, ethanol, and acetonitrile, hydrogen peroxide is used as an aqueous hydrogen peroxide solution comprising phosphoric acid or an alkali metal or ammonium salt of phosphoric acid, a chelating agent, which is a polyphosphonic acid or an alkali metal or ammonium salt thereof, is added to the aqueous hydrogen peroxide solution before it is mixed with solvent, and a mixture comprising olefin, solvent, and hydrogen peroxide with added chelating agent is continuously passed through a fixed bed of an epoxidation catalyst comprising a titanium zeolite.

2. The process of claim 1, wherein the aqueous hydrogen peroxide solution is mixed with at least 50% of the solvent used for reacting the olefin with hydrogen peroxide.

3. The process of claim 1, wherein the chelating agent is added in an amount of from $10^{-7}$ to $10^{-2}$ mol chelating agent per mol of hydrogen peroxide.

4. The process of claim 1, wherein the olefin is propene and the solvent is acetonitrile.

5. The process of claim 1, wherein the solvent is a methanol solvent.

6. The process of claim 1, wherein the mixture passed through the fixed bed of epoxidation catalyst comprises ammonia.

7. The process of claim 6, wherein the mixture comprises ammonia in an amount of from 100 to 3000 ppm based on the weight of hydrogen peroxide.

8. The process of claim 1, wherein the fixed bed epoxidation catalyst is placed in the tubes of a vertically arranged tube bundle reactor, chelating agent is added to an aqueous hydrogen peroxide stream before it is mixed with a solvent stream to form a mixed stream, and the mixed stream is distributed to the top of the tubes through orifices of a liquid distributor.

9. The process of claim 8, wherein the mixed stream is combined with the olefin before being distributed to the top of the tubes.

10. The process of claim 8, wherein the mixed stream and the olefin are distributed to the top of the tubes through orifices of two separate liquid distributors.

11. A process for the epoxidation of propene with hydrogen peroxide in the presence of a solvent, wherein the solvent is selected from the group consisting of methanol, ethanol, and acetonitrile, hydrogen peroxide is used as an aqueous hydrogen peroxide solution comprising phosphoric acid or an alkali metal or ammonium salt of phosphoric acid, a chelating agent, which is a polyphosphonic acid or an alkali metal or ammonium salt thereof, is added to the aqueous hydrogen peroxide solution before it is mixed with solvent, and a mixture comprising propene, solvent, and hydrogen peroxide with added chelating agent is continuously passed through a fixed bed of an epoxidation catalyst comprising a titanium zeolite.

12. The process of claim 11, wherein the aqueous hydrogen peroxide solution is mixed with at least 50% of the solvent used for reacting the olefin with hydrogen peroxide.

13. The process of claim 11, wherein the chelating agent is added in an amount of from $10^{-7}$ to $10^{-2}$ mol chelating agent per mol of hydrogen peroxide.

14. The process of claim 11, wherein the fixed bed epoxidation catalyst is placed in the tubes of a vertically arranged tube bundle reactor, chelating agent is added to an aqueous hydrogen peroxide stream before it is mixed with a solvent stream to form a mixed stream, and the mixed stream is distributed to the top of the tubes through orifices of a liquid distributor.

15. The process of claim 14, wherein the aqueous hydrogen peroxide solution is mixed with at least 50% of the solvent used for reacting the olefin with hydrogen peroxide.

16. The process of claim 15, wherein the chelating agent is added in an amount of from $10^{-7}$ to $10^{-2}$ mol chelating agent per mol of hydrogen peroxide.

* * * * *